United States Patent [19]

Douglas

[11] 4,381,788

[45] May 3, 1983

[54] METHOD AND APPARATUS FOR DETECTING APNEA

[76] Inventor: David W. Douglas, 9323 Alden, Lenexa, Kans. 66215

[21] Appl. No.: 238,813

[22] Filed: Feb. 27, 1981

[51] Int. Cl.³ .............................................. A61B 5/08
[52] U.S. Cl. .................................. 128/722; 128/782; 361/283; 361/291; 361/313
[58] Field of Search ............... 128/722, 718, 724, 780, 128/782; 361/283, 291, 313

[56] References Cited

U.S. PATENT DOCUMENTS

| | | |
|---|---|---|
| 3,324,848 | 6/1967 | Domeier et al. . |
| 3,325,799 | 6/1967 | Farris . |
| 3,533,095 | 10/1970 | Collins . |
| 3,631,438 | 12/1971 | Lewin . |
| 3,727,606 | 4/1973 | Slelaff . |
| 3,771,152 | 11/1973 | Dettling et al. . |
| 3,795,240 | 3/1974 | Frank . |
| 3,831,586 | 8/1974 | Petit . |
| 3,836,900 | 9/1974 | Mansfield . |
| 3,926,177 | 12/1975 | Hardway, Jr. et al. . |
| 3,942,513 | 3/1976 | Frank . |
| 3,950,799 | 4/1976 | Frank . |
| 4,033,332 | 7/1977 | Hardway, Jr. et al. . |
| 4,066,072 | 1/1978 | Cummins . |
| 4,146,885 | 3/1979 | Lawson, Jr. . |
| 4,320,766 | 3/1982 | Alihanka et al. ................ 128/722 X |
| 4,956,743 | 5/1976 | Geiszler et al. . |

FOREIGN PATENT DOCUMENTS 1307272 2/1973 United Kingdom .

Primary Examiner—Kyle L. Howell
Assistant Examiner—John C. Hanley
Attorney, Agent, or Firm—Kokjer, Kircher, Bradley, Wharton, Bowman & Johnson

[57] ABSTRACT

An apnea monitor having a capacitance type transducer pad providing a signal indicative of respiration. The resilient dielectric material between the capacitor plates is formed in two layers with the upper layer having a lesser spring constant to make the pad more sensitive around the periphery of the body to respond to respiratory motion while rejecting cardiovascular motion. The transduced signal is monitored and its gain is automatically adjusted to compensate for long term instability by a gain-set circuit arrangement having a time delay to assure that changes in the signal are not caused by apnea. A control voltage generated by the circuit operates the alarm without excessive time delay and is also used to provide a gain-set voltage for adjustment of the signal gain.

1 Claim, 5 Drawing Figures

METHOD AND APPARATUS FOR DETECTING APNEA

BACKGROUND OF THE INVENTION

This invention relates generally to respiratory physiology and deals more particularly with a method and apparatus for monitoring apnea.

In the field of respiratory physiology, it has long been known that post-operative patients and patients with brain damage and other debilitating injuries are susceptible to the sudden cessation of breathing which is known as apnea. Sudden infant death syndrome is caused by apnea and is triggered by an immaturity in the central nervous system that ordinarily corrects itself by the first birthday. Apneic episodes nearly always occur during sleep. Infants that are likely to be subject to sudden infant death syndrome are presently identified by considering a number of factors such as family history, premature birth, and the age and physical condition of the mother. In the intensive care nursery, likely apnea candidates are carefully monitored, and subsequent close monitoring in the home is usually recommended if any signs of susceptibility to apnea are observed in the nursery. It is not uncommon for an infant to first demonstrate apnea at about two months of age.

The various types of apnea monitors that have been proposed are essentially respiration monitors. Among their basic components, they include a transducer which senses respiration and provides a signal, an electronic circuit for conditioning the signal, and an alarm device which provides an alarm following an adjustable time delay after loss of signal. The alarm generates a noise that sometimes awakens the infant such that spontaneous resumption of breathing occurs. If the infant is not awakened, resuscitation is necessary.

Apnea monitors differ primarily in the type of transducer employed. Some monitors employ direct techniques which sense the flow of air in the airway. For active babies up to several months old, direct transducers of this type are impractical. The other type of transducer is an indirect type which detects the physical movement accompanying respiratory effort rather than ventilation itself. Indirect transducers can be either contact types or noncontact types.

Direct contact transducers require that electrodes or other sensing elements be attached directly to the torso or chest of the infant. This encumbers free movement and can cause skin irritation and related problems. Particularly with large infants such as those monitored in the home, it is common for the electrodes to fall off or be pulled off and for the infant to become entangled in the wires leading from the electrodes. Among the types of noncontact sensors that have been proposed are segmented pneumatic mattresses equipped with an anemometer for sensing the flow of air among the segments, mattresses filled with a conductive elastomer, Doppler ultrasound transceivers, and capacitance type transducers that are either incorporated into a rigid mattress or placed under the mattress. All of these noncontact transducers suffer from numerous problems that have detracted from their commercial success. Typically, they are small and/or rigid in order to focus on a limited area so that stability and reproductability can be achieved. However, this introduces problems relating to changes of position of the infant within the crib or bassinet.

Perhaps the most important problem associated with all existing apnea monitors is a lack of reliability. All known monitors are subject to false alarms when apnea does not occur and, even more importantly, they sometimes fail to give an alarm during apnea. Both contact and noncontact transducers are overly sensitive to the beating of the heart and movement of the great vessels, and both types of instruments sometimes interpret this "cardiovascular artifact" as respiration when there is actually an absense of respiration. As a result, the alarm is not given even though apnea has occurred.

Another serious problem with existing apnea monitors involves the manner of displaying whether there is normal breathing or an alarm condition and whether or not the instrument is functioning properly. Oscilloscope displays have been attempted but are so large and expensive as to be virtually prohibitive under most circumstances.

Since the incoming signal varies over a wide range, the gain during apnea should not be allowed to rise to a level that invites problems with artifact. If apnea should occur and the infant is awakened by the resulting alarm, there is no indication given by most existing instruments that there has been an apnea episode. The episode thus passes unnoticed by the parents or nurse.

In existing apnea monitoring instruments, the time delay of the alarm is commonly generated by using a timed zero-crossing technique. If the incoming signal is lost, the timer begins to run but is reset to zero if the signal should reappear before elapse of the time delay period which is typically about 15 seconds. If the infant should twitch during apnea, which is not uncommon, the timer is reset and the alarm is delayed accordingly. Thus, the time delay prior to giving an alarm can be extended such that the alarm is not sounded in sufficient time to either awaken the baby or alert the parents or nurse to the apnea episode.

SUMMARY OF THE INVENTION

The present invention is directed to an improved apnea monitor and has, as its primary goal, the provision of an improved method and apparatus for detecting apnean in a more accurate and reliable manner than has been achieved in the past. In accordance with the invention, a unique capacitor type transducer pad is constructed in a manner to respond to respiratory movement while rejecting cardiovascular artifact movement. Supression of the cardiovascular artifact is accomplished by forming the pad such that it is least sensitive where the body weight is greatest and most sensitive around the periphery of the body where respiratory effort is most pronounced. The pad is flexible so that it is able to readily withstand being folded and can be easily stored, it is soft and comfortable and is sensitive to respiration of the infant without picking up extraneous outside movement, and it is shielded from water and other liquids that could cause a short circuit.

Another important feature of the invention is the gain-set circuit which compensates for the long term instability and variation in the sensitivity of the transducer pad. The strength of the signal from the transducer can vary over a wide range even in the absense of apnea, particularly if the pad is moved between infants of different size and morphology, if the infant assumes a different position, or if the transducer has been folded, rolled up or otherwise deformed immediately prior to use. In any of these situations, the signal level can take up to several hours to stablize. The gain-set circuit corrects for such variations in the input signal strength by automatically adjusting the gain of the signal after delaying long enough to assure that the signal change is not caused by apnea.

The invention also includes an improved visual display in the form of a single row of light emitting diodes. Most of the LEDs are yellow and normally flash or blink in sequence in and out from the center of the row to provide an analog representation of the respiratory function. If apnea occurs, a cluster of red LEDs in the center of the row are energized to indicate an alarm condition, and they remain energized until manually reset. Thus, a visible sign remains to indicate that apnea has occurred even if the infant is aroused by the audible alarm and resumes breathing spontaneously. A pair of green LEDs at the opposite ends of the row indicate the status of the gain-set circuit and provide information indicating that the signal gain is proper.

The alarm trigger circuit is unique and is improved over the zero-crossing detection technique that can result in undue delay prior to the alarm being given. In contrast to the zero-crossing technique, the present invention has an alarm trigger circuit that generates a control voltage having a current proportional to the signal strength. The control voltage operates a current sensitive LED and its voltage is virtually constant over a wide range of input signals. The control voltage begins decaying exponentially when the input signal is lost due to apnea. When the decaying control voltage drops to the level of a time related voltage introduced into the alarm driver, the alarm is triggered and gives both a visible and audible indication of apnea. This control voltage technique for triggering the alarm assures that the alarm is merely delayed momentarily rather than completely reset if the infant should twitch during apnea.

DETAILED DESCRIPTION OF THE INVENTION

In the accompanying drawings which form a part of the specification and are to be read in conjunction therewith and in which like reference numerals are used to indicate like parts in the various views.

Figure 1:
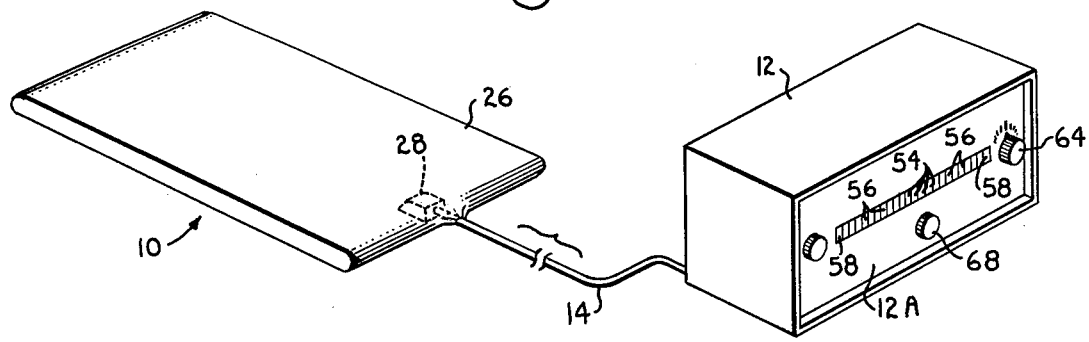
FIG. 1 is a perspective view of an apnea monitoring instrument constructed according to a preferred embodiment of the present invention.

With initial reference to FIG. 1, the apnea monitoring instrument of the present invention includes capacitance type transducer pad 10 and a cabinet 12 which contains the majority of the circuit elements and which has a visual display on its front panel 12A. A cord 14 extends from pad 10 and carries a plug (not shown) that may be inserted in a mating socket formed on the backside of cabinet 12.

Figure 2:
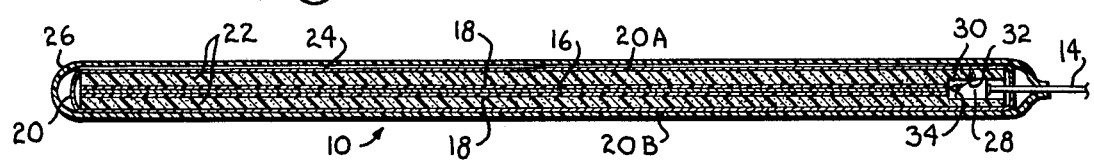
FIG. 2 is a fragmentary sectional view taken through the transducer pad included in the apnea monitor.
Figure 3:
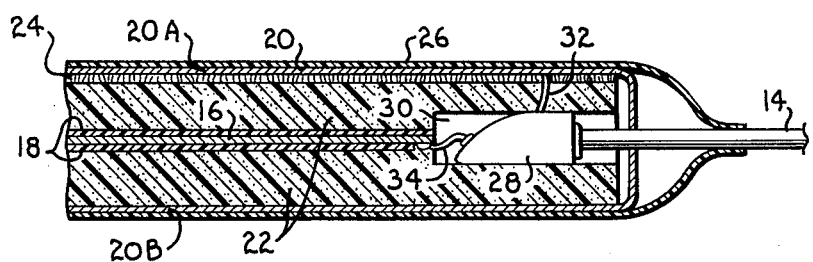
FIG. 3 is a fragmentary sectional view on an enlarged scale of one end portion of the transducer pad.

Referring additionally to FIGS. 2 and 3, the transducer pad 10 includes a flat inner conductor 16 which forms one capacitor plate of the transducer. The inner conductor 16 is flexible and is preferably formed of a polyester fabric which is embedded with aluminum. Two sheets of insulating film 18 adhere to the top and bottom surfaces of the inner conductors 16. The insulating sheets 18 protect the inner conductor from liquids that might cause a short circuit in the high resistant element. Preferably, sheets 18 are formed from a material such as polyurethane film or a similar substance.

Numeral 20 designates an outer conductor which is wrapped around the inner conductor 16 to provide an upper capacitor plate 20A spaced above and parallel to conductor 16 and a lower capacitor plate 20B spaced below and parallel to the inner conductor. The outer conductor 20 is flexible and is preferably formed of a polyester fabric embedded with aluminum. A pair of foam pads 22 are sandwiched between the inner conductor 16 and the upper and lower conductors 20A and 20B. Pads 22 provide the dielectric material of the capacitor and are constructed of a soft resilient material such as polyurethane foam. A thin layer 24 of napped material such as velour adheres to the upper surface of the upper foam pad 22. The upper portion 20A of the outer conductor 20 is located on top of layer 24. Layer 24 has a spring constant considerably less than that of the underlying foam pad 22.

In constructing pad 10, after the inner conductor 16 has been enclosed between the film sheets 18 and the inner assembly has been sandwiched between the foam pads 22, the velour layer 24 is applied to the upper pad and the outer conductor 20 is wrapped around the pad assembly. A flexible cover 26 contains the pad, and the pad cover 26 is constructed of a heat welded waterproof plastic material such as a polyurethane sheet. The underside of cover 26 provides controlled leakage to prevent pneumatic damping of the signal. In the assembled pad, the inner conductor 16 is parallel to portions 20A and 20B of the outer conductor 20 to provide parallel capacitor plates. The pad is generally rectangular and is sized to cover the entire bottom surface of a crib or bassinet.

A small electronic package 28 is located in a cavity 30 formed in the foam pads 22 near the upper edge of the pad. A wire 32 connects the electronic package 28 with the outer conductor 20 in order to apply a constant electrical charge on the outer plate of the capacitor. Another wire 34 connects the package with the inner conductor 16 in order to permit sensing of the charge which is induced on the inner plate and the voltage of the transduced signal. The cord 14 leads from the electronic package 28.

Figure 4:
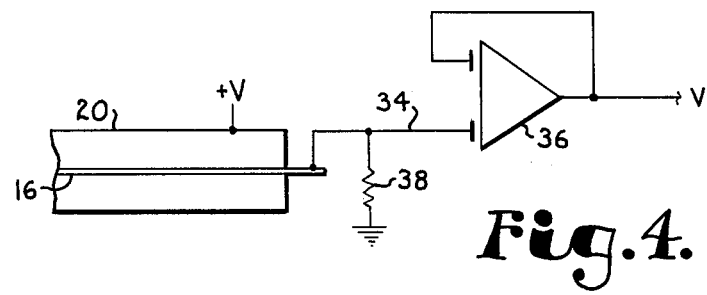
FIG. 4 is a partial schematic diagram of the circuit which produces a transduced signal indicative of the respiratory function.

The electronic package includes an electrometer type amplifier such as a field effect operational amplifier 36 (FIG. 4) having a very high resistance 38 to provide the ground return. Since the fixed charge Q which is placed on the outer conductor 20 is substantially constant, the sensed voltage output V of the preamplifier 36 changes in accordance with the relationship $\Delta V = Q/\Delta C$ in response to changes in the capacitance C due to movement accompanying the respiratory effort of an infant lying on pad 10. The output from the operational amplifier 36 thus provides a transduced signal indicative of respiration. The transducer requires an extremely high terminating resistance (typically 200 megohms), and it is thus preferred for the preamplifier to be housed within the transducer pad 10 in order to shield it from stray electrical fields.

Figure 5:
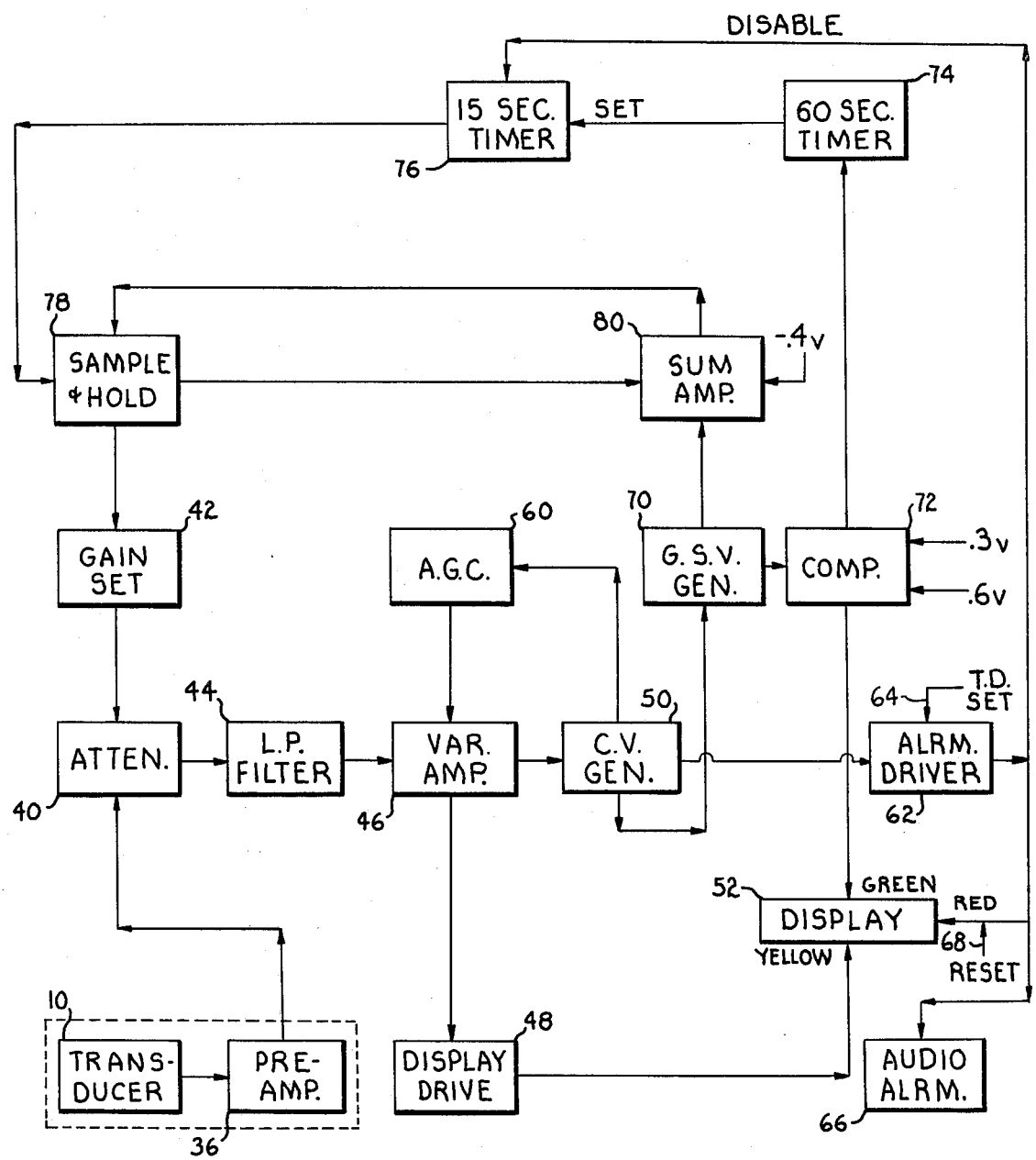
FIG. 5 is a block diagram of the complete electronic circuit included in the instrument.

Referring now to FIG. 5, the preamplifier 36 serves primarily to provide impedance transformation and also offers some amplification and low pass filtering. The output signal from the preamplifier is applied to an attenuator 40 which, along with the remaining components of the circuit, is housed in the cabinet 12. Since the preamplifier 36 provides a more than adequate signal, the attenuator 40 is utilized, although an amplifier could be used instead if necessary. The attenuator 40 includes an active circuit element such as an operational amplifier or another adjustable gain element having its gain determined by a gain set device 42 which may be an optical coupler or a field effect transistor.

The attenuated signal from the attenuator 40 is passed through an electronic filter 44 which, together with the filter in the preamplifier 36, limits the pass band frequencies to 0.4–1.25 Hz which characterizes infant respiration. Respiration rates outside of this frequency band are abnormal, and common artifacts (noise in the signal) other than cardiovascular artifact are outside of these limits. Most of the circuit gain is taken in a variable amplifier 46 which receives the signal from the filter 44.

The attenuator 40, filter 44 and variable amplifier 46 condition the incoming transduced signal. The conditioned signal is applied by the variable amplifier 46 to a display drive circuit 48 and also to a control voltage generator 50 which will subsequently be described. Display drive circuit 48 operates a display circuit 52 which controls a visual display located on the front panel 12A of cabinet 12.

As shown in FIG. 1, the visual display on panel 12A includes a horizontal row of light emitting diodes that includes in its center four red LEDs 54 that serve to indicate an alarm condition. Extending outwardly from both sides of the center red LEDs 54 are a number of yellow LEDs 56 which are connected in pairs that are symmetric about the center of the row. In other words, the second yellow LED to the left of center is connected with the second yellow LED to the right of center and so forth. The display circuit 52 lights the connectal pairs of yellow LEDs 56 in sequence such that yellow lights flash outwardly along the row on both sides of the center and, when the end of the row is reached, the yellow LEDs flash inwardly toward the center. The result is that the LEDs "swing" symmetrically inwardly and outwardly from the center to normally provide an analog signal indicative of respiration. A single green LED 58 is located at each end of the row.

Referring again to FIG. 5, the output from the variable amplifier 46 is applied to the control voltage generator 50 as previously indicated. The control voltage generator 50 generates a control voltage signal having a current which is proportional to the attenuated signal provided by the attenuator 40. This control voltage signal is applied to an automatic gain control circuit 60 which provides automatic gain control for the variable amplifier 46. Short term shifts in signal strength are thus corrected by the automatic gain control circuit to maintain the display "on scale."

The control voltage signal is also applied to an alarm driver 62 which receives an adjustable time related voltage (TD set) to provide an alarm time delay controlled by an adjustment knob 64 (FIG. 1) on the front panel of cabinet 12. The time delay can be adjusted up to 25 seconds by properly positioning knob 64. When the control voltage applied to alarm driver 62 drops to the level of the time related voltage introduced on the TD set line, an audio alarm 66 is triggered and provides an alarm noise to indicate apnea. The alarm signal is additionally applied to the display circuit 52 to energize the red LEDs 54 in the center of the display. Once the red LEDs 54 have been energized, they remain energized until manually reset by a reset button 68 located on the front panel of the cabinet.

The current of the control voltage signal generated by the control voltage generator 50 is sampled by a gain-set voltage generator 70 which produces a gain-set voltage that is extremely sensitive to changes in the level of the input signal. A gain-set voltage level of about 0.4 volts indicates a properly attenuated input signal in the preferred embodiment of the invention. The gain-set voltage feeds a comparitor circuit 72 which compares the voltage with established voltage limits defining a normal range of the gain-set voltage. For example, the voltage limits can be 0.3 volts and 0.6 volts in order to maintain the gain-set voltage within range. If the gain-set voltage is between the established limits, the comparitor 72 provides a signal to the display circuit 52 which effects constant energization of the green LEDs 58 on the opposite ends of the display row. This provides information indicating that the attenuator 40 is properly adjusted as to its gain.

If the gain-set voltage is outside of its normal range (0.3 volts–0.6 volts), the signal delivered by the comparitor 72 to the display circuit 52 causes the green LEDs 58 to initially flash and then become extinguished as the error increases. With the initial flashing of the green LEDs, comparitor 72 initiates a 60-second timer 74. After the elapse of a 60 second time delay, the 60-second timer 74 sets a 15-second timer 76. If an alarm signal is delivered by the alarm driver 62 within the 60 second time delay period, a disable signal is applied to the 15-second timer to disable the gain-set function, since it is not desirable to adjust the sensitivity in the presence of an alarm condition. If there is no alarm condition within the 60 second time delay, timer 74 resets itself and starts the 15-second timer 76 which switches a sample and hold circuit 78 into the "sample" mode.

The sample and hold circuit 78 controls the gain-set device 42 in order to adjust the gain of the active circuit element in attenuator 40. The sample and hold circuit 78 includes a memory which retains the previous signal level applied to the gain-set device 42. Immediately upon activation of the 15-second timer 76, the previous signal level applied to gain-set device 42 is transferred from the memory of the sample and hold circuit 78 and applied to a summation amplifier 80. The summation amplifier 80 receives the gain-set voltage generated by the gain-set voltage generator 70 and generates an error signal which is the difference between the ideal value of the gain-set voltage (0.4 volts) and the actual output voltage of the gain-set voltage generator 70. The voltage which is applied to the summation amplifier from the sample and hold circuit is added to or subtracted from the error signal, depending upon the polarity. The resultant signal is then applied to the sample and hold circuit 78. The gain set device 42 then adjusts the gain of attenuator 40 in a manner to return the gain-set voltage to within its normal range. At the end of the 15 second period established by timer 76, equilibrium is established, timer 76 resets, and the sample and hold circuit returns to the "hold" mode.

In operation, the apnea monitoring instrument detects apnea and provides both a visual and audio alarm indicitive thereof. When an infant or other patient lies on the transducer pad 10, the body weight distorts the inner conductor 16 slightly and the upper conductor 20A grossly, and also crushes the velour layer 24 between the body and the upper foam pad 22. Due to the body weight, very little movement of the outer conductor with respect to the inner conductor can occur directly under the body during respiration. However, around the periphery of the body where there is minimum body pressure, the velour layer 24 lifts the upper conductor 20A off of the surface of the upper pad 22 during respiration and there is thus considerable relative movement between the inner and outer conductors around the periphery of the body. As a consequence, the sensor pad is least sensitive where body weight is the greatest and where the effects of cardiovascular artifact are greatest. Conversely, the pad is most sensitive where the body weight is the least but where respiratory motion is most significant. Thus, during apnea, the transducer does not pick up cardiovascular motion and interpret such motion as respiration.

The transduced signal which results from respiratory effort is applied to the attenuator 40 after impedance matching in the preamplifier 36. The conditioned signal from the variable amplifier 46 is applied to the display drive circuit 48 which operates the display circuit 52 in a manner causing the yellow LEDs 56 to "swing" inwardly and outwardly in response to respiration. The automatic gain control circuit automatically adjusts the gain of the variable amplifier such that the conditioned signal has the proper amplitude to maintain the analog display "on scale".

If apnea should occur, the control voltage signal from the control voltage generator 50 immediately begins decaying exponentially and, when sufficient time has elapsed for it to drop to the level of the time related voltage entered into the alarm driver 62, the audio alarm 66 is triggered and the red LEDs 54 are energized on the display surface of the cabinet. The contrast between the swinging movement of the yellow LEDs and the constant energization of the red LEDs permits the condition of the infant to be ascertained with a quick glance at the display panel of the cabinet.

The audio alarm 66 can awaken the infant such that spontaneous resumption of breathing occurs. This terminates the audio alarm 66, but the red LEDs 54 remain energized until manually reset by the reset button 68. Therefore, the parents and hospital personnel are alerted to the fact that an apneic episode has occurred even in those situations where resuscitation is not necessary.

It is important to note that the alarm trigger circuit provides an adjustable time delay that is not objectionably prolonged by an active patient. Since the current of the control voltage signal is proportional to incoming signal strength and operates a current sensitive light emitting diode, the voltage of the control voltage signal is virtually constant at 1.4–1.5 volts over a wide range of signal level. When apnea occurs, the voltage immediately begins decaying in exponential fashion. Thus, if the infant should twitch during an apnea episode, the alarm is merely delayed momentarily rather than being completely reset. The exponential decay continues immediately after the twitch is terminated.

The gain-set circuit and related components act to correct the setting of the attenuator 40 from time to time to compensate for long term or unusual short term fluctuations that are not handled by the automatic gain control circuit. Also, the gain-set circuit maintains the incoming signal level at a prudently low value in order to set a limit on the gain level that can be achieved by the automatic gain control circuit during apnea. Thus, the sensitivity of the system to extraneous physical movement or other artifact is limited during apnea.

So long as the gain-set voltage remains within the normal range of 0.3 volts–0.6 volts, the sample and hold circuit 78 remains in the "hold" mode and the gain of attenuator 40 is unaffected. However, if the gain-set voltage departs from its normal range, the comparitor 72 initiates operation of the 60-second timer 74 and, if there is no alarm condition within 60 seconds (the maximum time delay for the alarm is 25 seconds), the sample and hold circuit is placed in the sample mode. Immediately, the most recent signal level applied to gain-set device 42 is transferred from memory to the summation amplifier 80 and is added to or subtracted from the error signal. The gain-set device 42 then adjusts the gain of attenuator 40 appropriately such that the gain-set voltage returns to its normal range. When equilibrium has been established after 15 seconds, the sample and hold circuit returns to the hold mode. If the change in the input signal is due to apnea, the alarm signal generated by alarm driver 62 disables the circuit and prevents adjustment of the gain of the attenuator.

It is thus apparent that the present invention provides an apnea monitoring instrument which is insensitive to cardiovascular artifact, primarily due to the unique construction of the transducer pad 10. Also, the circuit automatically adjusts the sensitivity in response to appreciable changes in the signal strength after first making certain that the change in signal strength is not due to an emergency condition. The visual display is improved in comparison to oscilloscope displays and other expensive displays that have been attempted in the past.

The control voltage provided by control voltage generator 50 is important to the sophisicated operation of the device in a number of respects. In cooperation with the automatic gain control circuit, the control voltage corrects for short term shifts in signal strength. The current of the control voltage signal is sampled by the gain-set voltage generator which in turn generates a gain-set voltage used to automatically update the attenuator stage 40. Also, the control voltage is used in the alarm trigger circuit to provide a superior means for establishing an alarm time delay that is not sensitive to twitches of the infant. Finally, the control voltage signal can be used in conjunction with an external chart recording device that provides a permanent record of apneic trends. The circuit can be used in other types of physiological monitoring such as monitoring of blood pressure where short term changes are often more important diagnostically than absolute values.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, I claim:

1. A method of monitoring a patient for apnea, said method comprising the steps of:

placing the patient on a transducer pad which functions as a capacitor having a pair of spaced apart capacitor plates;

effecting a small degree of relative movement of the capacitor plates when motion of the body occurs in the area near the center of the body of the patient, thereby providing a small change in the capacitance of the pad in response to body movement corresponding to cardiovascular motion which is concentrated near the center of the body;

effecting a larger degree of relative movement of the capacitor plates when motion of the body occurs in the peripheral area of the body of the patient, thereby providing a larger change in the capacitance of the pad in response to body movement corresponding to respiratory motion which is concentrated near the peripheral area of the body; and sensing the larger change in the capacitance of the pad while rejecting the small change in the capacitance, whereby body motion corresponding to respiratory motion is sensed and body motion corresponding to cardiovascular motion is rejected.

* * * * *